US007824906B2

(12) United States Patent
Murphy et al.

(10) Patent No.: US 7,824,906 B2
(45) Date of Patent: Nov. 2, 2010

(54) ANAEROBIC REACTOR AND CORRESPONDING METHOD FOR DIGESTING ORGANIC MATERIAL

(75) Inventors: Scott Murphy, Milwaukee, WI (US); Jon Forbort, Minneapolis, MN (US); Evan Nyer, Tampa, FL (US); Matt Shattuck, Milwaukee, WI (US); Wes May, Milwaukee, WI (US)

(73) Assignee: ARCADIS U.S., Inc., Highlands Ranch, CO (US)

( * ) Notice: Subject to any disclaimer, the term of this patent is extended or adjusted under 35 U.S.C. 154(b) by 662 days.

(21) Appl. No.: 11/780,194

(22) Filed: Jul. 19, 2007

(65) Prior Publication Data

US 2009/0023193 A1 Jan. 22, 2009

(51) Int. Cl.
*C12M 1/00* (2006.01)
*C12M 3/00* (2006.01)
(52) U.S. Cl. .................. 435/293.1; 435/300.1
(58) Field of Classification Search .............. 435/289.1, 435/290.3, 293.1, 300.1–303.1
See application file for complete search history.

(56) References Cited

U.S. PATENT DOCUMENTS

| | | | |
|---|---|---|---|
| 2,805,921 A * | 9/1957 | Schaumann | 423/613 |
| 2,941,928 A * | 6/1960 | Sanders et al. | 202/221 |
| 4,057,401 A * | 11/1977 | Boblitz | 48/111 |
| 4,951,415 A * | 8/1990 | Kawarabayashi et al. | 47/60 |
| H1149 H | 3/1993 | Wyman et al. | |
| 5,746,919 A | 5/1998 | Dague et al. | |
| 6,342,378 B1 | 1/2002 | Zhang et al. | |

(Continued)

FOREIGN PATENT DOCUMENTS

CA 2577844 3/2006

(Continued)

OTHER PUBLICATIONS

M. Kayhanian "Ammonia Inhibition in High-Solids Biogasification: An Overview and Practical Solutions", Center for Environment and Water Resource Engineeering, Dept. Of Civil Engrg., Univ. of California.

(Continued)

*Primary Examiner*—Walter D Griffin
*Assistant Examiner*—Shanta G Doe
(74) *Attorney, Agent, or Firm*—Nancy J. Flint, Attorney at Law, P.A.; Nancy J. Flint

(57) ABSTRACT

The present invention is an anaerobic reactor and preferably a vertically oriented plug flow anaerobic reactor for producing methane from various organic materials. The organic materials preferably have a high organic content. The reactor includes cutting members for cutting bridged or agglomerated material within the reactor. The present invention also includes a process for producing methane from an organic feed stock by continuously charging an organic material into the top portion of a vertically oriented vessel and rotating one or more cutting members at a sufficiently slow rate so that the cutting members cut through bridged or agglomerated material but do not substantially mix contents within the reactor, anaerobically digesting the organic material under mesophilic or thermophilic conditions to produce methane while allowing the organic material to propagate downward through the vessel in a plug flow-like manner and collecting methane gas produced from the anaerobic digestion of the organic material.

25 Claims, 5 Drawing Sheets

U.S. PATENT DOCUMENTS

Figure 1:
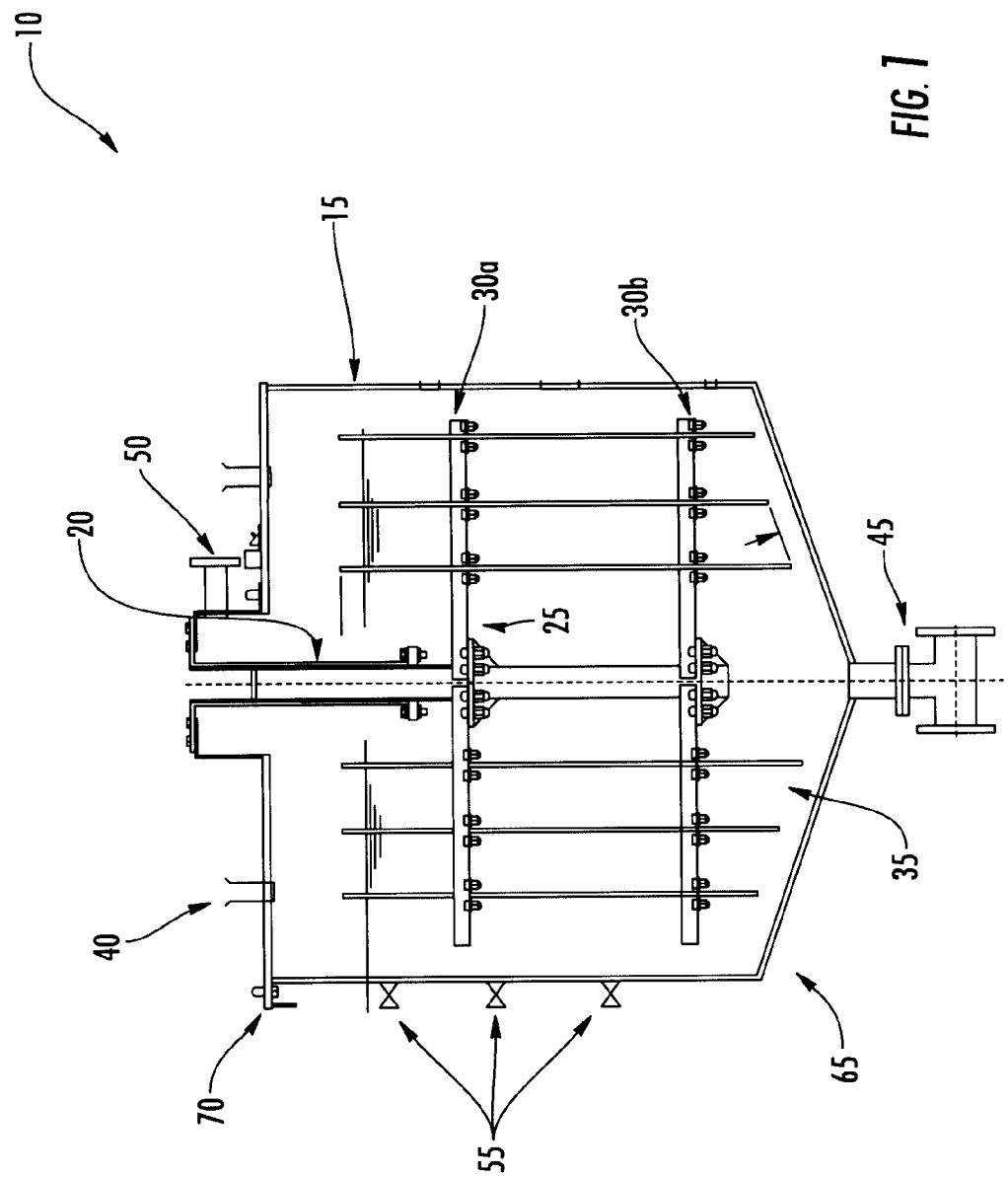

| | | | |
|---|---|---|---|
| 6,391,203 | B1 | 5/2002 | Fassbender |
| 7,045,063 | B2 | 5/2006 | Zhang et al. |
| 2007/0141691 | A1 | 6/2007 | Hirl |

FOREIGN PATENT DOCUMENTS

| | | | |
|---|---|---|---|
| KR | 2003063697 | * | 7/2003 |

OTHER PUBLICATIONS

Matthew P. Shattuck "An Assessment of the Applicability of Anaerobically Digesting Spent Grains from the Brewing Process at Miller Brewing Company, Milwaukee, WI," A Rept. submitted to Faculty of Milwaukee School of Engrg. in Partial Fulfillment of Requirements for MS Degree.

Karena Ostrem "Greening Waste: Anaerobic Digestion for Treating the Organic Fraction of Municipal Solid Wastes", Dept. of Earth and Environmental Engineering, Columbia Univ., May 2004.

* cited by examiner

ANAEROBIC REACTOR AND CORRESPONDING METHOD FOR DIGESTING ORGANIC MATERIAL

BACKGROUND OF THE INVENTION

1. Field of the Invention

The present invention relates generally to an anaerobic reactor for producing methane and a process for producing methane. More particularly, the present invention relates to a vertically oriented plug flow anaerobic reactor and processes for producing methane by anaerobically digesting organic materials.

2. Description of Related Art

The anaerobic digestion of various organic materials has been recognized as a means of reducing organic waste problems and producing methane for use as an alternative fuel source. Accordingly, a significant amount of work has been undertaken to develop a commercially viable means for anaerobically digesting various organic materials for the production of methane.

Conventional anaerobic treatment requires a feed having relatively low total solids content. More particularly, the operation of traditional anaerobic reactors are limited by high total solids in the feed or alternatively in the reactor itself upon digestion of the organic material. Specifically, prior anaerobic reactors have been limited to processing feeds having a total solids content less than about 10 percent, more typically between about 3 and 5 percent. As such, organic feeds having a high total solids content, namely about 10 percent or higher, must first be diluted with water prior to digesting. Furthermore, the exiting sludge from the reactor must then be dewatered. The costs associated with these operations and the reactor volumes necessary to achieve a commercially viable throughput of organic feed for digestion renders such conventional approaches economically unfeasible.

Due to the shortcomings of the more conventional reactors, additional research directed at developing a high solids anaerobic reactor (hereinafter "HSAR") for the anaerobic digestion of organic feeds having a total solids content above 10 percent has become an area of increasing importance. The primary focus for developing such a HSAR has been directed to configuring systems in which the high solids material is thoroughly mixed throughout the volume of the reactor in anticipation of increasing the interaction of the substrate, microorganisms and metabolic intermediates. To attain the level of mixing necessary to achieve substantial uniformity of the substrates, microorganisms and enzymes throughout the entirety of the reactor, these designs require an agitation means including a high power-high torque drive mechanism. Due to the high solids content within the reactor, the power costs and limitation of equipment that can produce the torque necessary for mixing economically viable volumes has limited such designs to small scale (e.g. less than 50,000 gallons) systems. As such, this approach does not provide a commercially viable anaerobic system for the production of methane.

Accordingly, there remains a need for a high solids anaerobic reactor capable of being implemented at a scale in which the production of methane is economically viable. Likewise, there is a need for an economically viable process for the production of methane via the anaerobic digestion of organic material.

BRIEF SUMMARY OF THE INVENTION

The present invention satisfies the aforementioned needs by providing a plug flow anaerobic reactor for producing methane and a process for the production of methane. Reactors in accordance with embodiments of the present invention preferably comprise a vertical vessel, a rotatable shaft extending downward through the vessel, and at least one cutting member directly or indirectly attached to the rotatable shaft; wherein the rotatable shaft is capable of being rotated at a sufficiently slow rate so that the at least one cutting member cuts through bridged or agglomerated material but does not substantially mix contents within the vessel.

In another aspect, the present invention provides a process for producing methane from an organic feed stock that preferably comprises: (a) continuously charging an organic material into the top portion of a vertically oriented vessel, wherein the vessel comprises a rotatable shaft extending downward through the vessel and includes at least one cutting member directly or indirectly attached to the rotatable shaft; (b) rotating the shaft at a sufficiently slow rate so that the at least one cutting member cuts through bridged or agglomerated material but does not substantially mix contents within the reactor; (c) anaerobically digesting the organic material under mesophilic or thermophilic conditions to produce methane while allowing the organic material to propagate downward through the vessel in a plug flow-like manner; and (d) collecting methane gas produced from the anaerobic digestion of the organic material.

Additionally, embodiments of the present invention provide a method for producing methane from an anaerobic reactor comprising: (a) feeding an organic material having a solids content ranging from about 20 to about 50 percent to a vertical vessel; (b) moving at least one cutting member through the organic material at a speed such that the cutting member cuts through bridged or agglomerated material but does not substantially mix the organic material within the reactor; (c) allowing the organic material to propagate downward through the vessel in a plug flow-like manner; (d) anaerobically digesting the organic material under mesophilic or thermophilic conditions to produce methane gas; and (e) collecting methane gas produced from the anaerobic digestion of the organic material.

BRIEF DESCRIPTION OF THE DRAWING(S)

Figure 2:
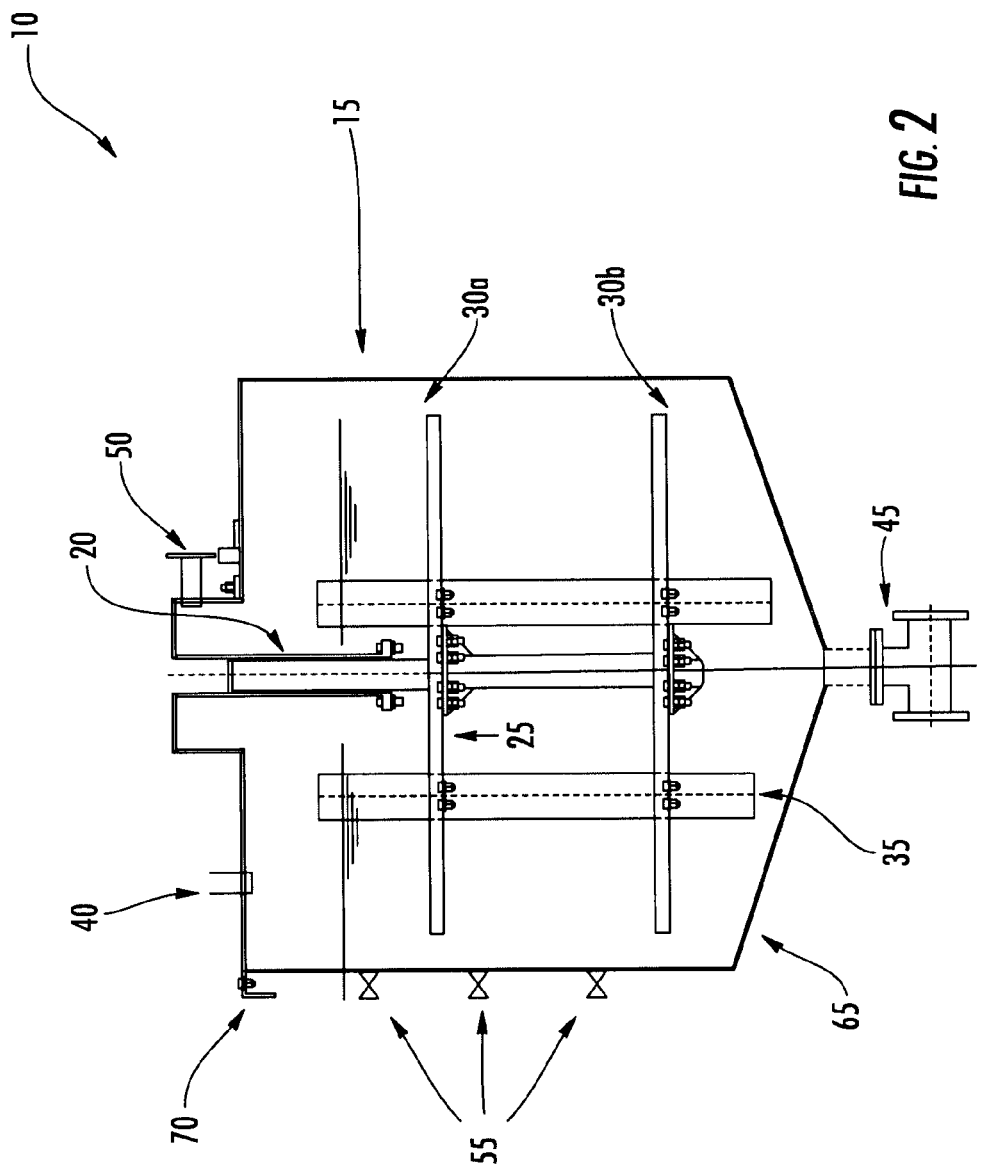
Figure 3:
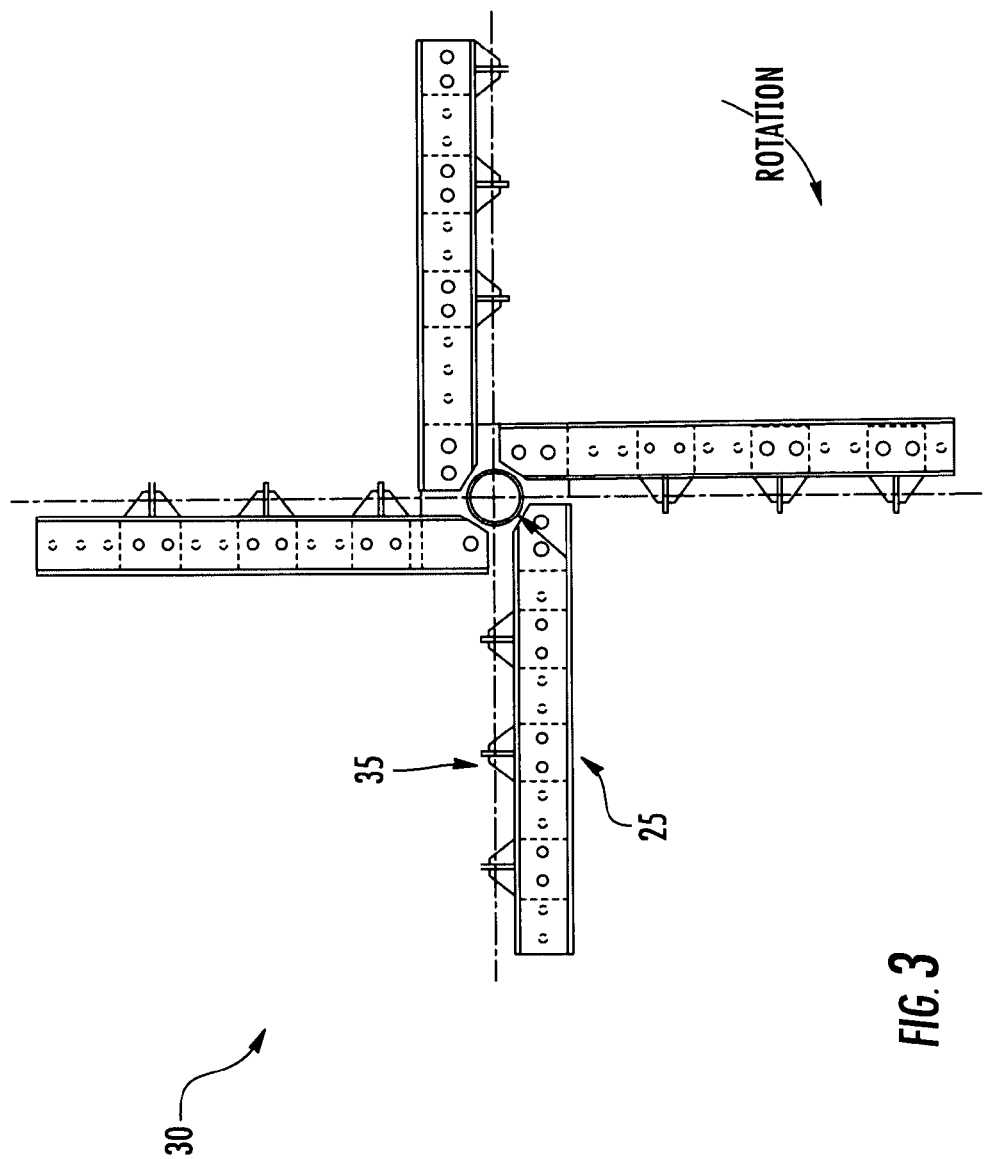
Figure 4:
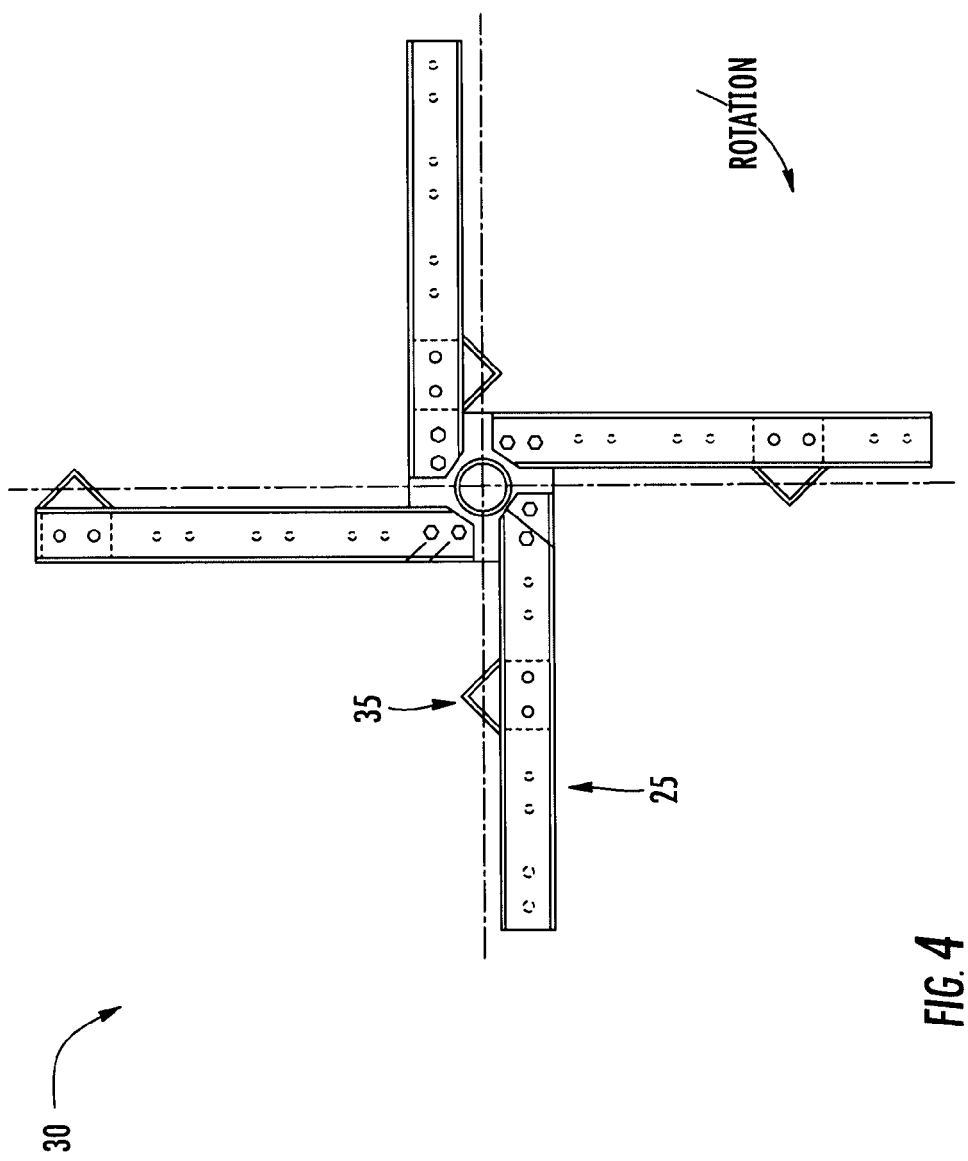

Having thus described the invention in general terms, reference will now be made to the accompanying drawings, which are not necessarily drawn to scale, and wherein:

FIG. 1. depicts a plug flow anaerobic reactor having multiple cutting members attached to corresponding arm members of multiple arm member sets according to one embodiment of the present invention;

FIG. 2. depicts a plug flow anaerobic reactor having a single cutting member attached to corresponding arm members of multiple arm member sets according to one embodiment of the present invention;

FIG. 3. depicts a single arm member set according to one embodiment of the present invention having multiple arm members each having multiple cutting members attached thereto; and FIG. 4. depicts a single arm member set according to one embodiment of the present invention having multiple arm members each having only a single cutting members attached thereto.

Figure 5:
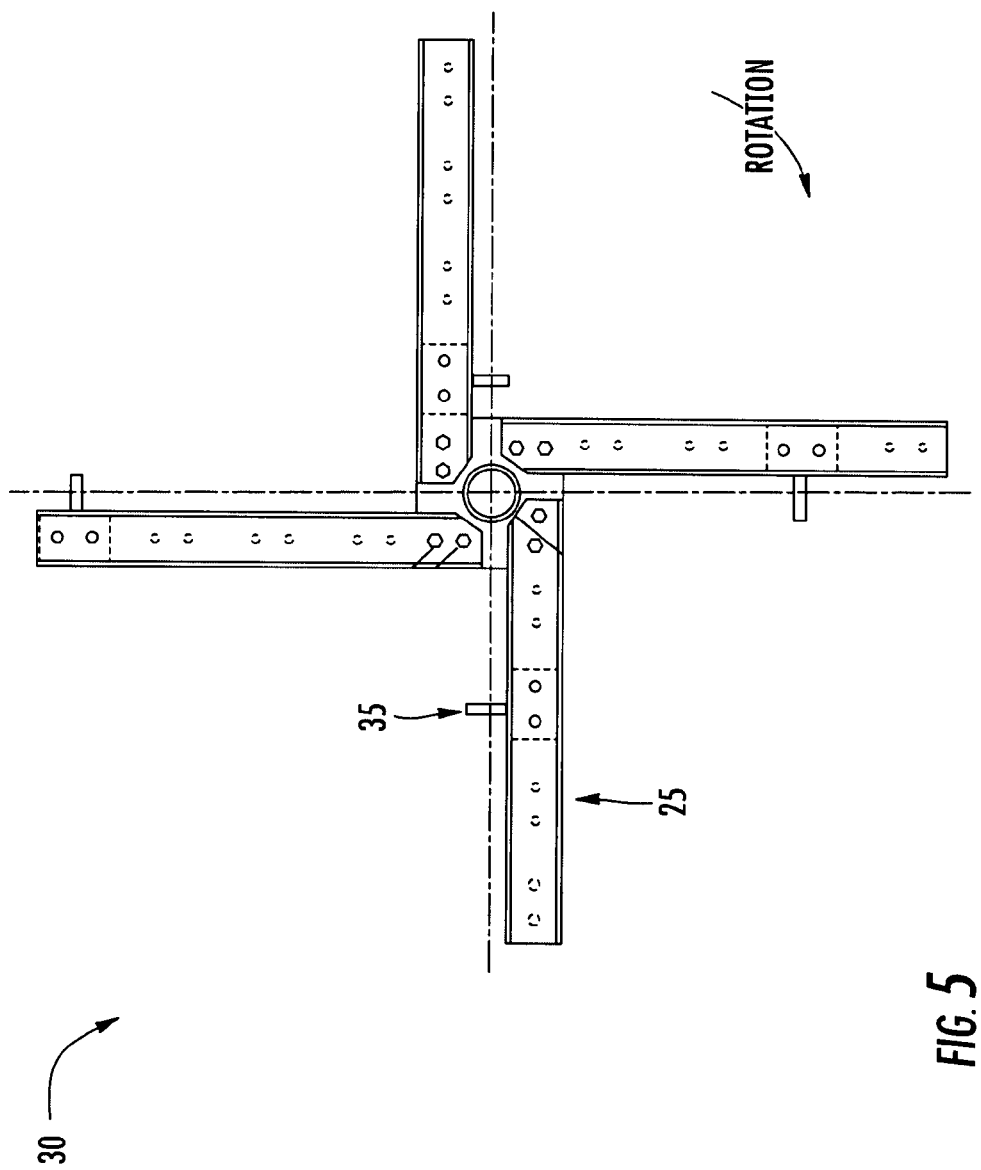

FIG. 5. depicts one alternative single arm member set having multiple arm members each having only a single perpendicular cutting members attached thereto.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

In one aspect of the present invention, a plug flow anaerobic reactor for digesting a wide variety of organic materials having a high total solids content (e.g. above about 10%) is provided. Although plug flow anaerobic reactors of the present invention are preferably for digesting organic materials having a high total solids content, organic materials having low total solid content can also be digested according to various embodiments of the present invention. Further, reactors according to embodiments of the present invention are suitable for large scale digestion of organic feed stocks such that the anaerobic digestion of organic materials enables the commercially viable production and collection of methane for use as an alternative fuel source.

Reactors of the present invention are preferably continuously charged with organic material for digestion. The organic material is preferably allowed to propagate through the reactor in a plug flow-like manner. In particular, the propagation of organic material through the reactor may be conceptualized as a thin coherent "plug" having a uniform composition traveling in the axial (e.g. downward) direction of the reactor, but with a differing composition with respect to leading and trailing plugs. As a "plug" flows through the reactor, the material within the "plug" may be thought of as being generally mixed in the radial direction but not in the axial direction (forward/downwards or backwards/upwards with respect to the vertical reactors of the invention).

FIG. 1 illustrates an anaerobic reactor 10 according to one embodiment of the invention. The reactor 10 includes a vertically oriented vessel 15. An organic material for digestion is continuously fed into the vertically oriented vessel 15 through a feed port 40 or ports located on or adjacent to a top portion 70 of the vessel. An effluent port 45 is located on or adjacent a bottom portion 65 of the vessel 15 for allowing digested sludge to exit the vessel.

A rotatable shaft 20 extends downward through the vessel 15 and typically includes multiple arm members 25 being attached directly or indirectly (e.g. through attachment to an intermediate member (not shown)) to the rotatable shaft. Preferably, the arm members 25 are attached such that they are substantially perpendicular to the rotatable shaft and radially extend from the shaft. A plurality of arm members 25 in the same horizontal plane with each other form an arm member set 30. In various embodiments, the reactor 10 includes multiple arm member sets 30, such that each arm member set is located in a different horizontal plane with respect to a drive mechanism (not shown) mounted on top of the reactor. Cutting members 35 are preferably attached either directly to the arm members 25 or indirectly (e.g. through attachment to an intermediate member or device which helps secure the cutting members) for cutting through bridged or agglomerated material within the vessel 15. Methane gas produced by the anaerobic digestion of the organic material is vented through a gas outlet port 50 located on or near the top of the vessel 15 and collected. Suitable collection methods would be understood to those skilled in the art.

The shaft 20 is rotated by a drive mechanism (not shown), preferably a low power—high torque drive mechanism, positioned on top of the vessel 15. The shaft 20 is rotated such that the arm members 25 and cutting members 35 do not substantially mix or agitate the contents within the vessel 15. Accordingly, the rate of rotation is sufficiently low so that the movement of the arm members 25 and cutting members 35 do not disturb the downward plug flow of the organic material through the vessel 15. For example, in one embodiment, the shaft is rotated at a rate so that tip speed of the cutting members ranges from about 1 ft/min to about 15 ft/min, more preferably from about 5 ft/min to about 12 ft/min, and even more preferably from about 8 ft/min to about 10 ft/min. The slow tip speed allows the cutting members 35 to cut through bridged or agglomerated material without substantially mixing or agitating the contents within the vessel 15 and disrupting the downward plug flow of the organic material through the vessel. Also by operating at a low tip speed, a low power-high torque drive mechanism can be used in embodiments comprising large scale reactors for the economically viable production of methane gas.

The cutting members 35 are designed such that upon slow rotation, they will cut through any bridged or agglomerated material within the vessel. In accordance with the invention, neither the cutting members 35 nor the arm members 25 significantly upset the downward plug flow of the organic material being digested. More particularly the movement of the arm members and cutting members should not promote more than a negligible amount of vertical or horizontal mixing of contents within the vessel. Further, the movement of the arm members and cutting members will facilitate the rising of methane gas through the vessel for collection. The rising methane may impart a small degree of mixing. However, the movement of the methane gas upward through and out the vessel does not significantly disrupt the downward plug flow of the organic material being digested. The cutting members 35 may be constructed from a variety of materials commonly used in anaerobic digestion processes. Such materials should preferably exhibit the necessary strength, durability and resistance to corrosion by the environment within the reactor. In one embodiment, the cutting members are constructed from stainless steel. In other embodiments, the cutting members can be constructed from variety suitable plastics. In one alternative embodiment, the cutting members are coated with a material, such as Teflon® or the like, to prevent build-up of organic material.

As illustrated in the Figures, the cutting members 35 according to various embodiments of the present inventions can comprise a variety of geometries. For instance, FIG. 4 illustrates cutting members 35 comprising an angular construction including a pointed tip. In various preferred embodiments, the cutting members comprise plates perpendicular to the arm members 25. The cutting members 35 (i.e. plates) according to these embodiments can include ¼"-1" steel plates having a length from about 3" to about 9". In one embodiment, the cutting members 35 comprise ½"-¾" steel plates having a length from about 5" to about 7". One such embodiment is illustrated in FIG. 5.

As illustrated in FIGS. 1 and 2, individual cutting members 35 can be attached to corresponding arm members 25 of multiple arm member sets 30. For example, the cutting members 35 can extend at least the distance between the arm member sets 30. Although not illustrated in FIGS. 1 and 2, the vessel 15 can include more than two arm member sets, and cutting members can extend at least the distance between the two arm member sets being furthest apart or can extend any intermediate distance between such two arm member sets. In a preferred embodiment of the invention, the cutting members 35 are attached either directly or indirectly to arm members 25 such that the cutting members are substantially parallel to the rotatable shaft 20. In such embodiments, the cutting members 35 are perpendicularly attached to the arm members 25.

As the organic feed material propagates downward through the vessel 15 in a plug flow-like manner, the organic material is anaerobically digested by microorganisms and preferably bacteria present in the vessel. Suitable bacteria would be readily ascertained by those skilled in the art. During digestion, biogas including carbon dioxide and methane are produced and vented out the gas outlet 50 for collection and can be further processed if desired to provide a more concentrated methane content. In various embodiments, the vessel 15 can include at least one sample port 55. For ease of operation, the vessel 15 preferably includes multiple sample ports 55 positioned such that during operation, an operator may obtain various samples from multiple locations within the vessel to adequately represent the efficacy of the digestion process. Furthermore, the sample ports 55 allow an operator to monitor the total solids or if desired the percent suspended solids throughout the vessel 15.

Although FIGS. 1 and 2 illustrate cutting members 35 attached only to two arm members 25, namely the cutting members are attached to a first arm member of a first arm member set 30a and also to a corresponding first arm member of a second arm member set 30b, the cutting members can be attached to three or more corresponding arm members from multiple arm member sets such that the cutting members extend at least the distance between the two arm member sets being furthest apart. Alternatively, the cutting members can be attached only to a single arm member.

In various embodiments of the present invention, the number of cutting members 35 attached to each arm member or corresponding arm members of multiple arm member sets comprises from about 5 to about 150; preferably from about 20 to about 140; more preferably from about 40 to about 120; most preferably from about 50 to about 100. In one alternative embodiment, the number of cutting members 35 attached to each arm member or corresponding arm members of multiple arm member sets comprises from about 25 to about 50.

FIGS. 3-5 illustrate embodiments including multiple arm members 25 oriented such that each individual arm member is substantially perpendicular to the arm members on either side. However, in alternative embodiments, the arm members are attached to the rotatable shaft such that individual arm members are not perpendicular to the arm members on either side. Despite FIGS. 3-5 showing arm member sets 30 having four individual arm members 25, various alternative embodiments include only one arm member while others include many more arm members (e.g. more than four). Furthermore, the individual arm members within an arm member set can be positioned in any configuration within a single plane.

In one embodiment, the arm member set or sets comprise from 1 to 4 arm members (i.e. 1, 2, 3 or 4). In one alternative embodiment, each arm member set comprises at least 4 arm members; preferably from 5 to about 10 arm members.

As illustrated in FIGS. 1 and 3, the plug flow anaerobic reactor 10 includes arm members 25 having multiple cutting members 35 attached thereto. Specifically, FIGS. 1 and 3 show embodiments having three cutting members 35 attached to each arm member 25, although each arm member can include numerous cutting members in accordance with the invention. In some embodiments, each arm member 25 or corresponding arm members of arm member sets 30 can include cutting members 35 attached from about every 0.5 ft. to about every 2 ft. Further, FIG. 1 illustrates an embodiment in which several cutting members 35 are attached both to an arm member 25 of an upper arm member set 30a and a corresponding arm member of a lower arm member set 30b such that the cutting members are parallel to the rotatable shaft 20. Although the cutting members 25 are preferably substantially parallel to the rotatable shaft 20, the cutting members 35 can be attached such that they are not parallel to the rotatable shaft 20.

As illustrated in FIGS. 2 and 4, the cutting members 35 can each be attached to a different arm member 25 of an upper arm member set 30a and to a corresponding arm member of a lower arm member set 30b. The cutting members 35 are positioned such that none of the cutting members are located the same distance from the rotatable shaft 20. In this particular embodiment, each cutting member 35 is substantially parallel to the rotatable shaft 20 and extends at least the distance between the arm member sets 30. However, the cutting members 35 can be attached at various other degrees in relation to the rotatable shaft 20. For example, one or more cutting members can be attached to an arm member of an upper arm member set and a corresponding arm member of a lower arm member set such that the point of attachment at the upper arm member is a greater distance from the rotatable shaft than that of the lower arm member, or vice versa.

In one alternative embodiment, the anaerobic reactor 10 includes a recycle line (not shown) connected to the effluent port 45 such that an operator may optionally recycle at least a portion of the bacteria and solids content within the reactor for the anaerobic digestion of the organic material within the vessel 15. Preferably, the recycled bacteria are recycled from a location adjacent the bottom portion 65 of the vessel (e.g. from effluent port 45) and mixed with fresh incoming feed to aid in the digestion of the organic feed stock. However, the recycling and mixing of the bacteria with incoming feed should be accomplished in a manner in which substantial mixing or agitation of the contents within the vessel is avoided. In particular, the recycling and mixing of the bacteria with fresh feed should not disturb the plug flow of the material in the reactor. There are multiple approaches known in the art for minimizing the disruption of contents within a vessel upon the addition of an incoming stream. For example, according to one embodiment of the present invention the bacteria stream for recycling can be mixed with fresh incoming feed in a mixing tank located outside and separate from the reactor. Once the bacteria and fresh feed are adequately mixed, this mixture is charged into the top portion 70 (e.g. via the inlet ports(s) 40) of the reactor for digestion.

The anaerobic reactor of the present invention is suitable for the large scale production of methane gas under either mesophilic or thermophilic conditions. Specifically, the design of the vertically oriented plug flow anaerobic reactor according to embodiments of the present invention enables the successful operation of anaerobic reactors for the production of methane utilizing reactors comprising a volume from about 200,000 to about 1,500,000 gallons, preferably from about 400,000 to about 1,400,000, more preferably from about 700,000 to about 1,300,000 gallons, and most preferably from about 900,000 to about 1,250,000 gallons.

According to alternative embodiments of the present invention, the volume can comprise from about 50,000 gallons to about 200,000 gallons. In various embodiments, the reactor volume comprises from about 75,000 gallons to about 175,000 gallons. In one alternative embodiment, the reactor volume comprises from about 100,000 gallons to about 150,000 gallons. In yet another embodiment, the reactor volume comprises between about 110,000 gallons to about 140,000 gallons.

The large scale reactors of the present invention are well suited for the anaerobic digestion of organic feed stocks having a high total solids content, but can also be used for the digestion of organic feed stocks having a low solids content. The reactors of the present invention can be utilized for the anaerobic digestion of an organic feed stock having a total solids content comprising from about 10 to about 50 percent or preferably from about 25 to about 40 percent. In other embodiments the total solids content comprises from about 20 to about 50 percent. In one alternative embodiment, the total solids content comprises from about 15 to about 35 percent. In yet another embodiment, the total solids content comprises from about 20 to about 30 percent. In one preferred embodiment of the present invention, the total solids content of the organic feed stock comprises from about 25 to about 35 percent.

In various alternative embodiments, the total solids content of the organic feed stock within the reactor comprises from about 10 to about 50 percent or preferably from about 25 to about 40 percent. In other embodiments the total solids content comprises from about 20 to about 50 percent. In one alternative embodiment, the total solids content comprises from about 15 to about 35 percent. In yet another embodiment, the total solids content comprises from about 20 to about 30 percent. In one preferred embodiment of the present invention, the total solids content of the organic feed stock comprises from about 25 to about 35 percent.

Organic materials suitable for digestion according to the present invention preferably have a high solids content. A few examples of suitable organic feed stocks include, but are not limited to, agricultural by-products, spent distillers grain (i.e. Distillers Dried Grains with Solubles) or more preferably wet distillers grain with or without solubles. Additional organic feed stocks include waste products from the production of beer, wine, pharmaceuticals, and chemicals, where microorganisms are used to produce the desired compound. Further, agricultural waste products from the wood industry, paper industry, and lawn and garden maintenance are suitable organic feed stocks.

The residence time for the anaerobic digestion of organic feed stocks to produce methane according to embodiments of the present invention can vary depending on the nature of the feed as well as the conditions within the reactor. In one embodiment, the residence time comprises from about 5 days to about 30 days. Under thermophilic conditions in accordance with the present invention, the residence time of the organic material preferably comprises from about 3 days to about 10 days and more preferably from about 5 days to about 8 days. Under mesophilic conditions in accordance with the invention, the residence time preferably comprises from about 15 days to about 30 days and more preferably from about 20 days to about 25 days.

According to various alternative embodiments of the present invention, a process for producing methane from an organic feed stock further includes controlling the total solids within the vessel itself. This may be accomplished in numerous ways, for example by obtaining samples from various locations in the vessel via sample ports to monitor the solids throughout the vessel and making appropriate adjustments to the operation of the reactor. Alternatively, the amperage of the drive mechanism can be monitored. Depending on the feed stock, controlling the solids within the vessel itself may lead to smoother and more efficient operation of the reactor. For example, the digestion of some organic feed stocks having high levels of soluble organic components could potentially generate solids in the reactor. In one alternative embodiment, the percent suspended solids within the reactor can be controlled.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A plug flow anaerobic reactor for producing methane, comprising:
   (a) a vertical vessel;
   (b) a rotatable shaft extending downward through said vessel; and
   (c) at least one cutting member directly or indirectly attached to said rotatable shaft;
   wherein the rotatable shaft is configured to rotate at a sufficiently slow rate so that the at least one cutting member cuts through bridged or agglomerated material but does not substantially mix contents within the vessel.

2. The reactor of claim 1, wherein the rotatable shaft further comprises at least one arm member directly or indirectly attached to the rotatable shaft; wherein said cutting member is directly or indirectly attached to the at least one arm member at an angle that allows the cutting member to cut through bridged or agglomerated material without substantially mixing contents within the vessel.

3. The reactor of claim 2, wherein said arm member is attached to said rotatable shaft and is substantially perpendicular to said rotatable shaft and said cutting member is attached to the at least one arm member is substantially perpendicular to said at least one arm member.

4. The reactor of claim 2, wherein the at least one arm member comprises a plurality of arm members each attached substantially perpendicular to the rotatable shaft and at the same distance from a drive mechanism operatively connected to the rotatable shaft and mounted on the top of the reactor; wherein the plurality of arm members define an arm member set.

5. The reactor of claim 4, further comprising a plurality of arm member sets; wherein each arm member set is located at a different distance from the drive mechanism.

6. The reactor of claim 5, wherein the at least one cutting member is attached to a first arm member of a first arm member set and to a corresponding first arm member of a second arm member set such that the at least one cutting member is substantially parallel to the rotatable shaft and extends at least the distance between the arm member sets.

7. The reactor of claim 5, wherein the at least one cutting member comprises a plurality of cutting members; wherein each cutting member is attached to a different arm member of a first arm member set and to corresponding arm members of a second arm member set such that each cutting member is substantially parallel to the rotatable shaft and extends at least the distance between the arm member sets.

8. The reactor of claim 7, wherein each group of corresponding arm members comprise a plurality of cutting members.

9. The reactor of claim 7, wherein each group of corresponding arm members comprise one cutting member positioned such that none of the cutting members are located the same distance from the rotatable shaft.

10. The reactor of claim 1, further comprising at least one feed port located adjacent the top of the vessel and at least one effluent port located adjacent the bottom of the vessel.

11. The reactor of claim 10, wherein the vessel includes bacteria and further comprises a recycle loop; wherein bacteria from the bottom portion of the reactor can be mixed with incoming feed adjacent a top portion of the vessel.

12. The reactor of claim 1, wherein the capacity of the vessel ranges from about 900,000 to about 1,250,000 gallons.

13. The reactor of claim 1, wherein the rotatable shaft is driven by a low power—high torque drive mechanism.

14. A process for producing methane from an organic feed stock, comprising:
(a) continuously charging an organic material into the top portion of a plug flow anaerobic reactor, the reactor comprising a vertical vessel; a rotatable shaft extending downward through the vessel; and at least one cutting member directly or indirectly attached to the rotatable shaft;
(b) rotating the shaft at a sufficiently slow rate so that the at least one cutting member cuts through bridged or agglomerated material but does not substantially mix contents within the reactor;
(c) anaerobically digesting the organic material under mesophilic or thermophilic conditions to produce methane while allowing the organic material to propagate downward through the vessel in a plug flow-like manner; and
(d) collecting methane gas produced from the anaerobic digestion of the organic material.

15. The process of claim 14, wherein the rotatable shaft further comprises at least one arm member attached to the rotatable shaft and substantially perpendicular to the rotatable shaft and wherein said cutting member is attached to the at least one arm member and is substantially perpendicular to the at least one arm member.

16. The process of claim 14, wherein said charging step comprises charging an organic material having a total solids content ranging from about 20 to about 50 percent.

17. The process of claim 16, wherein said charging step comprises charging an organic material having a total solids content ranging from about 25 to about 40 percent.

18. The process of claim 14, wherein said charging step comprises charging a feed comprising spent distillers grain.

19. The process of claim 14, wherein the vessel includes bacteria and the process further comprises recycling and mixing bacteria from the bottom portion of the reactor with incoming feed adjacent the top portion of the reactor.

20. The process of claim 15, wherein said rotating step comprises rotating the shaft at a rate so that the tip speed of the at least one cutting member ranges from about 5 to about 12 ft/min.

21. The process of claim 14, wherein the residence time for the organic material ranges from about 5 to about 30 days.

22. A method for producing methane from a plug flow anaerobic reactor, comprising:
feeding an organic material having a solids content ranging from about 20 to about 50 percent to a plug flow anaerobic reactor, the reactor comprising a vertical vessel; a rotatable shaft extending downward through the vessel; and at least one cutting member directly or indirectly attached to the rotatable shaft;
moving the at least one cutting member through the organic material at a speed such that the cutting member cuts through bridged or agglomerated material but does not substantially mix the organic material within the reactor;
allowing the organic material to propagate downward through the vessel in a plug flow-like manner;
anaerobically digesting the organic material under mesophilic or thermophilic conditions to produce methane gas; and
collecting methane gas produced from the anaerobic digestion of the organic material.

23. The method of claim 22, wherein said moving step comprises rotating a rotatable shaft extending along a longitudinal axis of the vessel and directly or indirectly attached to said at least one cutting member.

24. The method of claim 22, wherein said rotating step comprises rotating the rotatable shaft at a rate such that the tip speed of the at least one cutting member ranges from about 8 to about 12 ft/min.

25. The method of claim 22, wherein said feeding step comprises feeding an organic material that comprises spent distillers grain.

* * * * *